(12) United States Patent
Federspiel et al.

(10) Patent No.: US 11,832,806 B2
(45) Date of Patent: Dec. 5, 2023

(54) NEAR BONE SUTURE BUTTON

(71) Applicant: Acumed LLC, Hillsboro, OR (US)

(72) Inventors: Joshua P. Federspiel, Portland, OR (US); Gretchen Hinton, Hillsboro, OR (US); Steven Morgan, Greenwood Village, CO (US); Selene Parekh, Durham, NC (US); Alastair Younger, Vancouver (CA); Steve Crawford, Carlton, OR (US)

(73) Assignee: Acumed LLC, Hillsboro, OR (US)

( * ) Notice: Subject to any disclaimer, the term of this patent is extended or adjusted under 35 U.S.C. 154(b) by 413 days.

(21) Appl. No.: 17/016,807

(22) Filed: Sep. 10, 2020

(65) Prior Publication Data
US 2021/0068809 A1    Mar. 11, 2021

Related U.S. Application Data

(60) Provisional application No. 62/898,836, filed on Sep. 11, 2019.

(51) Int. Cl.
| | |
|---|---|
| *A61B 17/04* | (2006.01) |
| *A61B 17/68* | (2006.01) |
| *A61B 17/00* | (2006.01) |

(52) U.S. Cl.
CPC ........ *A61B 17/0401* (2013.01); *A61B 17/683* (2013.01); *A61B 2017/00367* (2013.01);
(Continued)

(58) Field of Classification Search
CPC .... A61B 2017/0404; A61B 2017/0406; A61B 2017/681; A44B 1/00–24
See application file for complete search history.

(56) References Cited

U.S. PATENT DOCUMENTS

| | | | | |
|---|---|---|---|---|
| 4,587,693 | A | * 5/1986 | Osumi | ..... A44B 1/08 24/111 |
| 5,566,430 | A | * 10/1996 | Cheng | ..... A44B 1/08 24/456 |

(Continued)

OTHER PUBLICATIONS

International Search Report corresponding to related International Patent Application No. PCT/US2021/049414 dated Dec. 14, 2021, 3 pages.

(Continued)

*Primary Examiner* — Phong Son H Dang
(74) *Attorney, Agent, or Firm* — K&L Gates LLP

(57) ABSTRACT

Suture buttons are disclosed for fixing two bones together. The suture buttons may enable surgeons to more easily and effectively implement a suture button technique, such as to repair syndesmosis injuries in ankles. A first suture button includes a pulley peg extending from a button head. The pulley peg may be positioned with a bone hole upon installation of the first suture button, which may help protect suture and help reduce potential patient discomfort. The second suture button helps facilitate the second suture button flipping into place upon deployment from a button inserter. Each of the first and second provided suture buttons may help reduce friction between the respective buttons and suture during an installation procedure. The first and second provided suture buttons may be used together in a surgical procedure or individually with other suitable buttons or anchors.

9 Claims, 14 Drawing Sheets

(52) U.S. Cl.
CPC ............. *A61B 2017/0404* (2013.01); *A61B 2017/0409* (2013.01); *A61B 2017/681* (2013.01)

(56) References Cited

U.S. PATENT DOCUMENTS

| | | | |
|---|---|---|---|
| 11,109,855 | B2 | 9/2021 | Shoshtaev et al. |
| 11,426,154 | B2* | 8/2022 | Niver ................. A61B 17/0401 |
| 2006/0241694 | A1* | 10/2006 | Cerundolo ......... A61B 17/1778 |
| | | | 606/232 |
| 2009/0271954 | A1* | 11/2009 | Kurita ..................... A44B 1/24 |
| | | | 24/90.1 |
| 2011/0172682 | A1 | 7/2011 | Brady et al. |
| 2012/0203249 | A1 | 8/2012 | Schmidt et al. |
| 2013/0172944 | A1 | 7/2013 | Fritzinger et al. |
| 2016/0089131 | A1* | 3/2016 | Wade .................... A61B 17/84 |
| | | | 606/232 |
| 2018/0008255 | A1* | 1/2018 | Fallin ................. A61B 17/0485 |
| 2018/0085110 | A1 | 3/2018 | Earhart et al. |
| 2018/0249998 | A1* | 9/2018 | Chavan .............. A61B 17/0487 |
| 2018/0280066 | A1* | 10/2018 | O'Connor ............. A61B 17/80 |
| 2020/0038010 | A1* | 2/2020 | Zakhary ............. A61B 17/7053 |
| 2020/0289109 | A1* | 9/2020 | Chavan ............ A61B 17/06166 |
| 2020/0306047 | A1* | 10/2020 | Boileau ................. A61F 2/2846 |
| 2021/0315325 | A1* | 10/2021 | LeCompte ............. A44B 1/185 |

OTHER PUBLICATIONS

International Written Opinion corresponding to related International Patent Application No. PCT/US2021/049414 dated Dec. 14, 2021, 8 pages.

International Search Report corresponding to related International Patent Application No. PCT/US2021/049446 dated Dec. 22, 2021, 3 pages.

International Written Opinion corresponding to related International Patent Application No. PCT/US2021/049446 dated Dec. 22, 2021, 10 pages.

International Preliminary Report corresponding to related International Patent Application No. PCT/US2021/0449414 dated Mar. 23, 2023, 10 pages.

International Preliminary Report corresponding to related International Patent Application No. PCT/US2021/049446 dated Mar. 23, 2023, 8 pages.

* cited by examiner

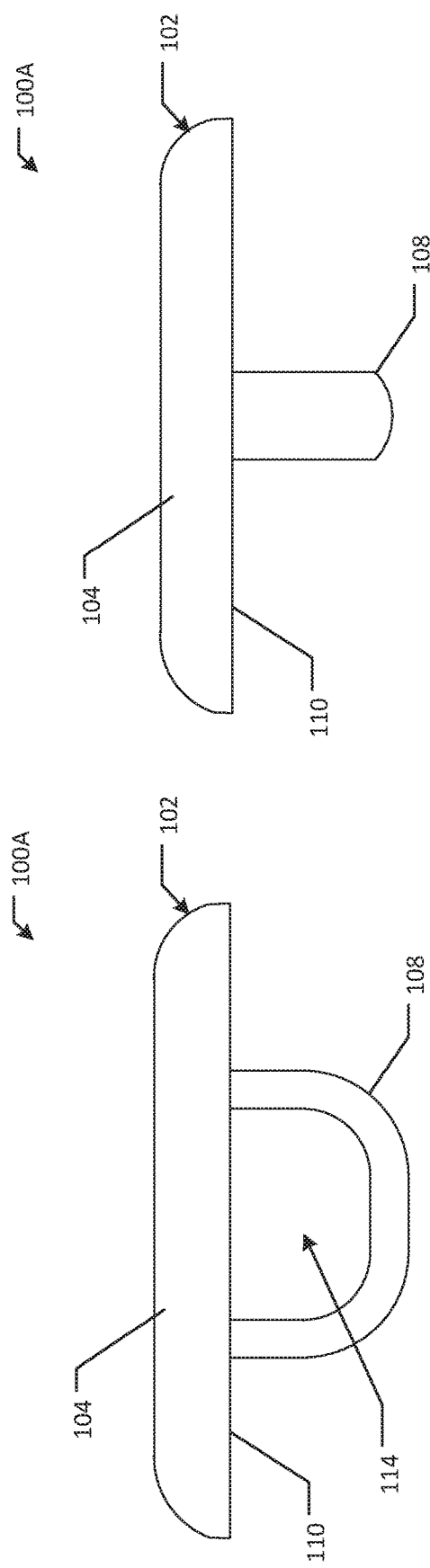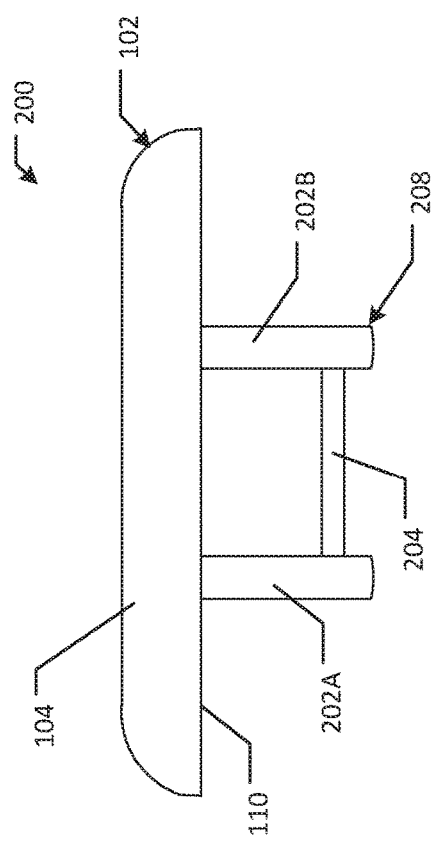

NEAR BONE SUTURE BUTTON

PRIORITY CLAIM

The present application claims priority to and the benefit of U.S. Provisional Application 62/898,836, filed Sep. 11, 2019, the entirety of which is herein incorporated by reference.

BACKGROUND

In various instances, patients may suffer injuries that require securing a first or near bone to a second or far bone in order to help the patient recover from the injury. Injuries to the ankle joint may be one such type of injury. The ankle joint is composed of two bones, the tibia and fibula, which are held together by the distal tibiofibular syndesmosis. In some instances, such as after ankle injuries, the syndesmosis can be torn, leaving a gap between the tibia and fibula. Syndesmotic injuries should be repaired if found torn or unstable in order to prevent ankle instability and subsequently reduce the risk of ankle osteoarthritis.

One method to secure a near bone to a far bone is the suture button technique. The suture button technique includes deploying a bone-securing construct that includes a first button coupled to a second button with suture. The suture may be tensioned to secure the near bone to the far bone. For example, to repair syndesmotic injuries, the suture button technique involves two buttons that hold the fibula (e.g., near bone) and tibia (e.g., far bone) together with suture that connects the two buttons through a drilled bone hole in the fibula and tibia. The buttons are typically put into place with a needle and pull-through sutures or with a button inserter.

Typical buttons for use in the suture button technique, however, have a number of drawbacks. Buttons for applying pressure to the near bone must anchor suture while also enabling the suture's ends to be pulled or tensioned in order to increase tension in the suture between the near bone button and the far bone button. As the suture is pulled or tensioned it must move or slide relative to the two buttons. Typical near bone buttons, however, may be constructed such that an undesired amount of friction is generated between the near bone button and the suture. For instance, typical near bone buttons may have multiple individual openings for different portions or ends of suture. The individual openings may restrict movement of the suture, creating friction. In other instances, typical near bone buttons may have an opening for the suture sized such that the suture is similarly restricted, creating friction. If friction is too great it may cause damage to the suture that requires the surgeon to start the procedure over, or that may cause the suture to fail prior to the patient recovering. An undesired amount of friction may also make it more difficult for the surgeon to perform the procedure. For example, the suture may get caught on an edge while the surgeon is tensioning the suture.

In addition, typical near bone buttons may extend out from the near bone an undesired amount after installation. This may cause patients a greater level of discomfort than if the near bone button was more flush with the near bone.

Buttons for applying pressure to the far bone may be transported through a bone hole and then adjusted so that they do not travel back through the bone hole. Adjusting a far bone button may involve deploying the far bone button from a button inserter, the deployment causing the far bone button to alter its orientation. Typically, however, such deployment may involve forcing the far bone button away from the inserter to give the far bone button enough space to change it orientation. The amount of space needed may make it difficult in some instances to easily and effectively deploy the far bone button, such as when tissue (e.g., skin) pushes against the far bone button and resists its changing orientation.

In addition, far bone buttons anchor suture that couples a far bone button to a near bone button. The suture must move relative to the far bone button as the suture is tensioned to install the far bone button and near bone button. Typical far bone buttons may generate a greater than desired amount of friction between a typical far bone button and the suture. For instance, many typical far bone buttons include at least two holes through which the suture moves, with friction generated between each hole and the suture. Such typical configurations with at least two holes may also cause the suture to wrap around itself or twist when loaded into or deployed from a button inserter.

Accordingly, a near bone button that solves the above drawbacks is desired. Additionally, a far bone button that solves the above drawbacks is desired.

SUMMARY

The presently disclosed suture button, system, and method generally relate to surgery techniques to hold two bones together. More specifically, suture buttons are disclosed that enable surgeons, or any other suitable healthcare provider, to more easily and effectively implement the suture button technique, such as to repair syndesmosis injuries in ankles. A first suture button is disclosed that is constructed to interface with a nearest bone (e.g., a fibula bone) as part of the suture button technique to secure a near bone and a far bone. A second suture button is disclosed that is constructed to interface with a farthest bone (e.g., a tibia bone) as part of the suture button technique to secure the near bone to the far bone. A surgeon may use both the provided first suture button and the provided second suture button when performing the suture button technique to repair a syndesmosis injury. Alternatively, a surgeon may use the provided first suture button with another suitable suture button or anchor, or may use the provided second suture button with another suitable suture button or anchor.

Throughout this disclosure, the first suture button will be referred to as a fibula button and the second suture button will be referred to as a tibia button, though it should be appreciated that the provided first suture button and the provided second suture button may be used to secure together bones other than the fibula and tibia.

In an example, a suture button for aiding in the fixation of two bones includes a head and a pulley peg. The suture button's head includes a top surface, a bottom surface, and a first opening extending through the head from the top surface to the bottom surface. The pulley peg is elongated from a first end to a second end. Each of the pulley peg's ends are connected to or integral with the head's bottom surface so as to form a second opening between the pulley peg and the head's bottom surface.

In an example, a system includes a first suture button or anchor, a second suture button, and a button inserter. The second suture button is coupled by suture to the first suture button or anchor. The second suture button includes a head and a pulley peg. The second suture button's head includes a top surface, a bottom surface, and a first opening extending through the head from the top surface to the bottom surface. The pulley peg is elongated from a first end to a second end. Each of the pulley peg's ends are connected to or integral with the head's bottom surface so as to form a second opening between the pulley peg and the head's bottom surface. The button inserter deploys the first suture button or anchor and the second suture button. A middle portion of the suture is positioned through the second suture button's second opening. Each of the suture's ends are positioned through the second suture button's first opening. Tensioning the suture's ends tensions the suture between the first suture button or anchor and the second suture button subsequent to deployment from the button inserter.

In an example, a method of securing two bones together includes forming a bone hole through a first bone and a second bone. A first suture button or anchor is then inserted, via a button inserter, through the bone hole such that the first suture button or anchor exits on the other side of the bone hole. The first suture button or anchor is coupled by suture to a pulley peg of a second suture button. The second suture button includes a head and a pulley peg. The second suture button's head includes a top surface, a bottom surface, and a first opening extending through the head from the top surface to the bottom surface. The pulley peg is elongated from a first end to a second end. Each of the pulley peg's ends are connected to or integral with the head's bottom surface so as to form a second opening between the pulley peg and the head's bottom surface. A middle portion of the suture is positioned through the second suture button's second opening. Each of the suture's ends are positioned through the second suture button's first opening.

The first suture button or anchor and the second suture button may be deployed from the button inserter. The ends of the suture may be tensioned such that the first suture button or anchor contacts the second bone and the second suture button contacts the first bone. The suture may then be secured.

BRIEF DESCRIPTION OF THE DRAWINGS

FIGS. 2A and 2B illustrate cross-sectional side views of a fibula button having a rounded pulley peg, according to one aspect of the present disclosure.

FIG. 2C illustrates a cross-sectional side view of a fibula button having a non-rounded pulley peg, according to one aspect of the present disclosure.

DETAILED DESCRIPTION

Figure 1A:
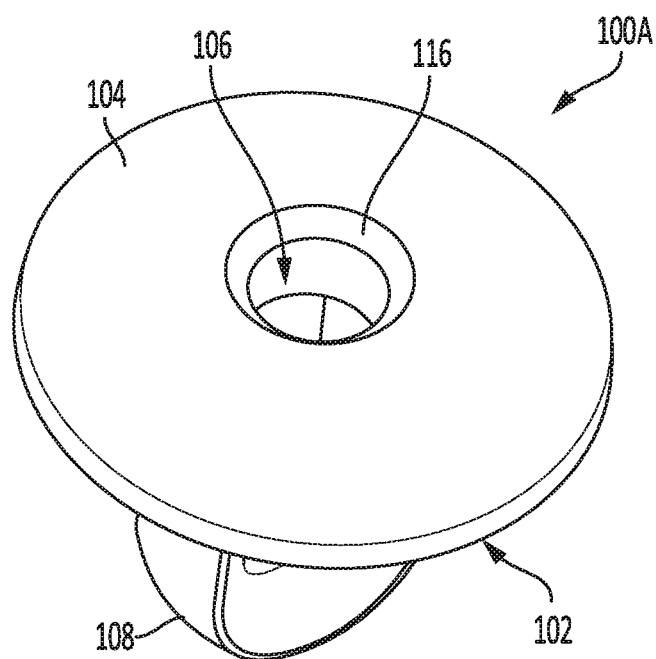
FIGS. 1A and 1B illustrate perspective views of a fibula button having a head with a circular opening, according to one aspect of the present disclosure.

The presently disclosed suture buttons, system, and method generally relate to surgery techniques to hold two bones together. More specifically, suture buttons are disclosed that enable surgeons, or any other suitable healthcare provider, to more easily and effectively implement the suture button technique, such as to repair syndesmosis injuries in ankles. In one example, a surgeon may use a button inserter to deploy the buttons. In such an example, a first presently disclosed suture button is adapted to contact the near bone as part of the bone-securing construct. A second presently disclosed suture button is adapted to be transported through a bone hole formed in the near bone and far bone and then to contact the far bone as part of the bone-securing construct. Throughout this disclosure, the first suture button will be referred to as a fibula button and the second suture button will be referred to as a tibia button, though it should be appreciated that the provided first suture button and the provided second suture button may be used to secure together any two bones other than the fibula and tibia.

A surgeon may use both the provided fibula button and the provided tibia button when performing the suture button technique, such as to repair a syndesmosis injury. Alternatively, a surgeon may use the provided fibula button with another suitable suture button or anchor, or may use the provided tibia button with another suitable suture button or anchor.

In some instances, the provided fibula button construction reduces friction between the fibula button and suture during the installation of the fibula button as compared to typical near bone buttons by including large spaces in the provided fibula button through which suture can travel without encountering metal components of the fibula button. The provided fibula button may include a head and a pulley peg extending from the head. The head includes a single opening and the space between the pulley peg and the head is a second opening. Each of the openings is sized such that multiple strands of suture may move freely through the openings. Suture may move more freely through larger spaces, which reduces friction between portions of suture and between suture and the fibula button. The provided fibula button may additionally include various curved or smooth or chamfered surfaces to further reduce friction.

In some instances, the fibula button's pulley peg is sized such that it may be inserted within a bone hole. Inserting the pulley peg within a bone hole helps lock the fibula button in place to a greater degree than if the fibula button merely rested on a bone's surface. Inserting the pulley peg within the bone hole also enables the fibula button to be more flush to the near bone than typical near bone buttons. Additionally, the pulley peg being positioned within the bone hole upon installation enables tensioned suture to be maintained inside of the bone rather than on the bone surface where the suture would be more exposed to other tissues. The fibula button may therefore help decrease potential patient irritation or discomfort that may arise from an installed button or suture protruding from one of the patient's bones. The fibula button may also help protect the tensioned suture from potential damage. In addition, having the tensioned suture maintained within the bone enables a surgeon to cut the free ends of the suture flush to the fibula button's surface without the risk of cutting the tensioned suture.

The provided tibia button construction may reduce friction between the tibia button and suture during installation of the tibia button as compared to typical far bone buttons. For instance, the provided tibia button includes a single, large opening for suture to pass through. The single, large opening reduces the number of possible contact points between the tibia button and the suture as compared to typical buttons that include multiple openings for the suture. The tibia button may also include various curved or smooth or chamfered surfaces to further reduce friction. The provided tibia button further helps prevent the suture from winding about itself when the tibia button is loaded into or deployed from a button inserter by directing the suture to a single side relative to the button inserter.

The provided tibia button may also be configured such that it is prevented from rotating or laterally translating when loaded into a button inserter. The provided button insertion system may also help facilitate the tibia button flipping upon deployment from a button inserter. The tibia button includes a chamfered end that, when loaded into a button installer, faces towards the suture that couples the tibia button to a second button (e.g., a fibula button). The natural inclination of the tibia button to rotate towards the direction the chamfered end is facing in addition to tension from the suture facilitates the tibia button flipping in that direction. Further, to deploy the tibia button, the button inserter may include a pusher rod that extends just beyond the tip of the button inserter to push the tibia button out of the tip within which the tibia button is loaded. The flipping facilitation aspects of the button insertion system enable the tibia button to flip close to the button inserter tip with little space in between.

The closeness with which the tibia button flips to the button inserter, and the aspects that help facilitate the tibia button flipping, generate a strong flipping force that helps the tibia button overcome opposing forces from tissue (e.g., skin) that may push against the tibia button. Further, each of these aspects may help increase the ease of deploying the tibia button as compared to at least some typical button insertion systems by helping ensure the tibia button changes its orientation, or flips, in a target or desired direction. Additional advantages of the provided fibula button and the provided tibia button will be apparent from the following description of the figures.

Figure 1B:
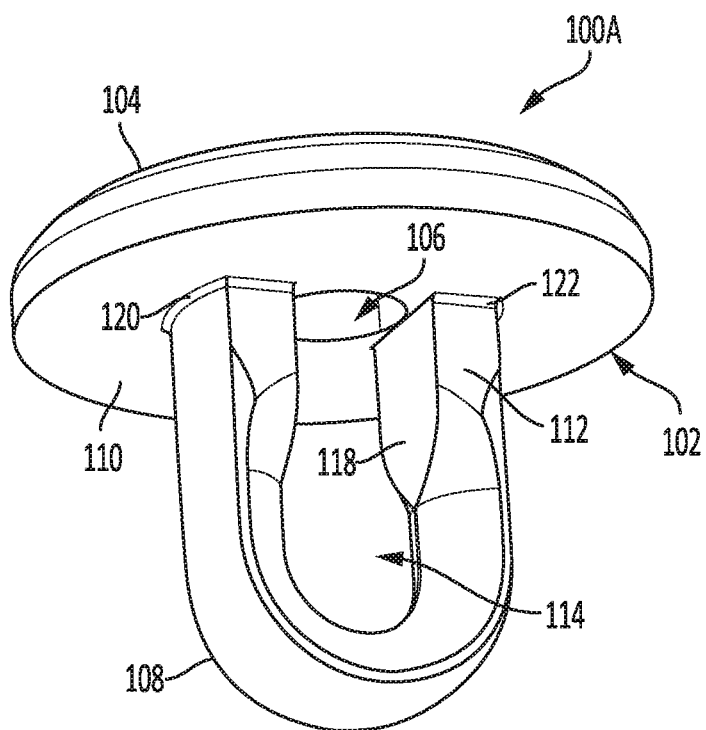

FIGS. 1A and 1B illustrate perspective views of an example fibula button 100A. The example fibula button 100A includes a button head 102 and a pulley peg 108 extending from the button head 102. An opening 114 is formed between the button head 102 and the pulley peg 108. The button head 102 includes a top surface 104 and a bottom surface 110. In various aspects, the top surface 104 may be rounded to help prevent damage to surrounding tissue when the fibula button 100A is installed in a patient. In some aspects, the bottom surface 110 may be flat as illustrated. The button head 102 also includes an opening 106 that extends through the button head 102 from the top surface 104 to the bottom surface 110. The opening 106 is sized such that it can accommodate multiple strands of suture moving through the opening 106. In some instances, the opening 106 may be sized large enough such that a suture knot may be positioned within the opening 106. The top surface 104 may include a chamfer 116 that leads to the opening 106. The chamfer 116 may help reduce friction between the button head 102 and suture moving through the opening 106. In various instances, the opening 106 may have a circular cross-section as illustrated.

Figure 1C:
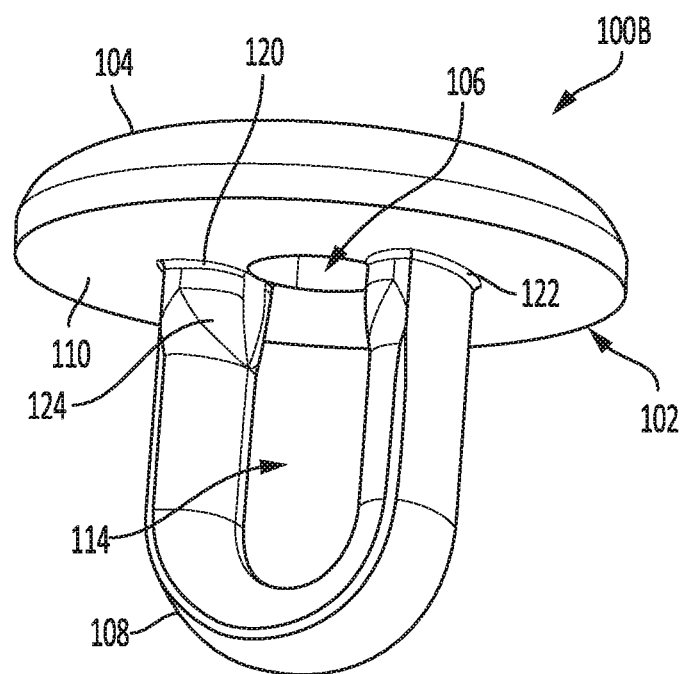
FIG. 1C illustrates a perspective view of a fibula button having a pulley peg with rounded ends, according to one aspect of the present disclosure.

In various aspects, the pulley peg 108 is elongated from a first end 120 to a second end 122. The first end 120 and the second end 122 may be connected to or integral with the bottom surface 110 of the button head 102. In some instances, the pulley peg 108 may include a flat surface 118 at each of its ends 120 and 122. The flat surfaces 118 may help guide suture through the opening 106. In some instances, the pulley peg 108 may include a flat surface 112 at each of its ends 120 and 122. In other instances, the pulley peg 108 may include a curved surface 124 at each of its ends 120 and 122, as illustrated in FIG. 1C as part of example fibula button 100B. The curved surface 124 may help reduce friction between the pulley peg 108 and suture moving towards and through the opening 106.

Figure 1D:
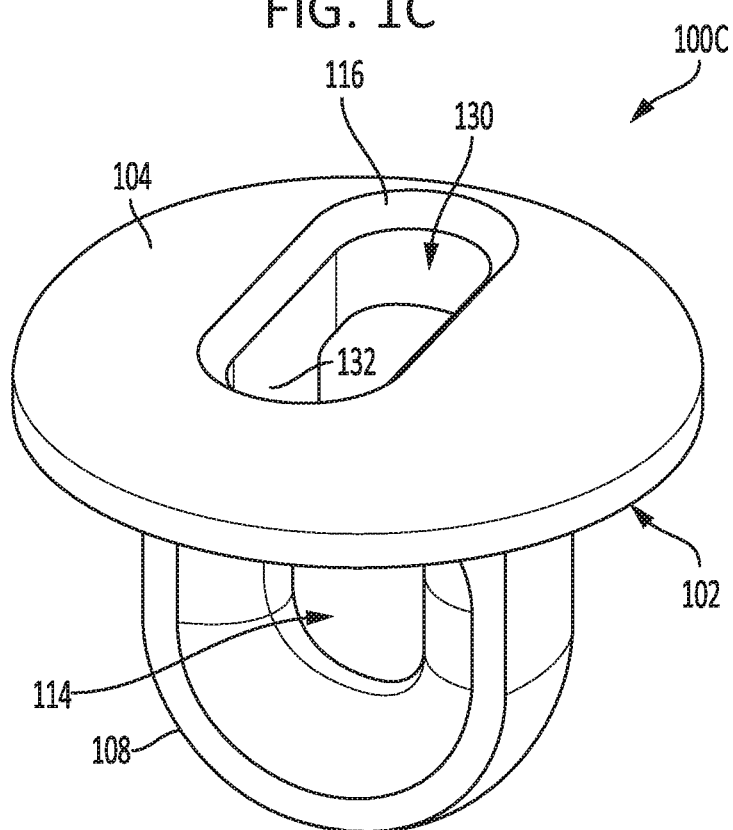
FIG. 1D illustrates a perspective view of a fibula button having a head with a chamfer on its top surface leading to its opening, according to one aspect of the present disclosure.

In various instances, the opening 106 may have suitable cross-sections other than circular. For example, the opening 106 may have a cross-section that is pill-shaped, rectangular with rounded corners, oval, or other suitable shapes. FIG. 1D illustrates an example fibula button 100C with a button head 102 having an opening 130 with an elongated or pill-shaped cross-section. The pill-shaped cross section of the opening 130 may help reduce friction between suture strands and/or between suture strands and the button head 102 by providing additional space for the suture to move freely. For instance, ends of the suture strand(s) may move through the opening 130 while remaining outside of the outer bounds of the pulley peg 108. Stated differently, the ends of the suture strand(s) do not have to move inward to a central opening (e.g., the opening 106) which may cause friction between portions of the suture strand(s). In addition, the pill-shaped opening 130 may be large enough such that a suture knot may be positioned within pill-shaped opening 130.

In various instances, the pill-shaped opening 130 may be substantially perpendicular to the pulley peg 108 as illustrated. Stated differently, the pill-shaped opening 130 includes a long end and a short end, and a plane extending through a central portion of the two ends 120 and 122 of the pulley peg 108 is substantially perpendicular to the long end. This substantially perpendicular configuration enables the pulley peg 108 to maintain a narrower width than if the ends 120 and 122 of the pulley peg 108 were on the outside of the long end of the opening 130. The narrower width enables the pulley peg 108 to fit within a narrower bone hole.

In various instances, the innermost portion of the pulley peg 108 and an inner portion of the button head 102 (e.g., the portion forming the opening 130) share a continuous surface 132. Stated differently, the inner surface of the button head 102 that forms the opening 130 continues directly into the pulley peg 108. This is in contrast to there being a space on the bottom surface 110 between the opening 130 and the ends 120 and 122 of the pulley peg 108. Eliminating this space between the opening 130 and the ends 120 and 122 of the pulley peg 108 helps eliminate edges that may increase friction between suture and the fibula button 100C.

Figure 1E:
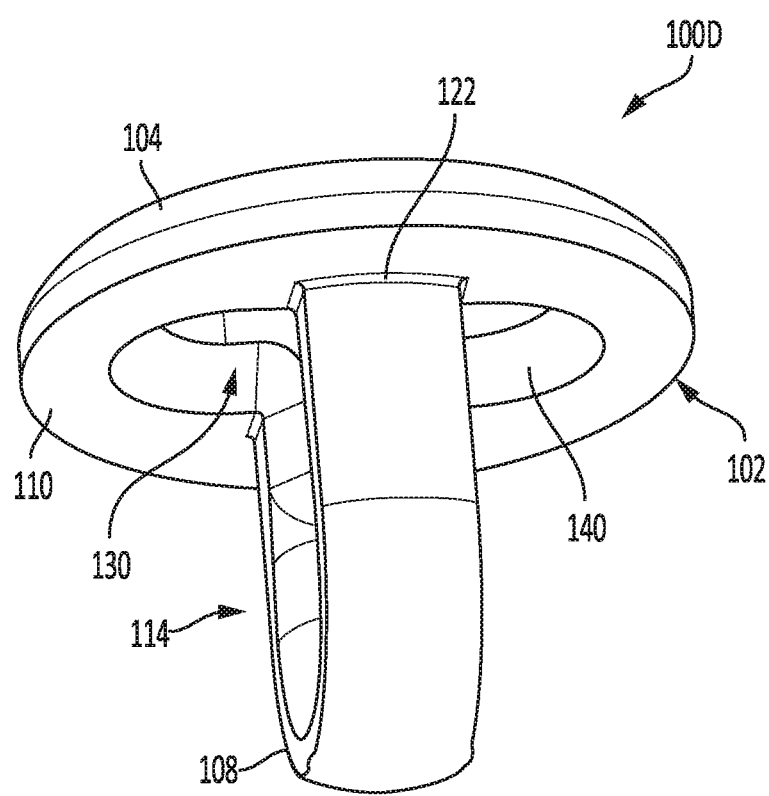
FIG. 1E illustrates a perspective view of a fibula button having a head with a chamfer on its bottom surface leading to its opening, according to one aspect of the present disclosure.

In some aspects, the bottom surface of the provided fibula button's button head may include a chamfer leading to the button head's opening. For example, FIG. 1E illustrates an example fibula button 100D in which the bottom surface 110 of the button head 102 includes a chamfer 140 leading to the opening 130. The chamfer 140 may help reduce friction between the button head 102 and suture moving through the opening 130.

FIGS. 2A and 2B illustrate respective side views, rotated ninety degrees with respect to one another, of the example fibula button 100A. As will be discussed in more detail below, the pulley peg 108 is configured to secure suture (e.g., multiple suture strands and/or multiple portions of a single suture strand). For example, in FIG. 2B a free end of a suture strand may enter the opening 114 on one side and exit the opening 114 on the other side such that when both free ends of the suture strand are pulled away from the fibula button 100A, the pulley peg 108 secures the suture strand. In other aspects of the present disclosure, the pulley peg 108 may take other suitable shapes extending outward from the bottom surface 110 that allow it to secure one or more suture strands. For example, FIG. 2C illustrates an example fibula button 200 that includes a pulley peg 208. The pulley peg includes two legs 202A and 202B connected by a crossbar 204. In some instances, the legs 202A, 202B and the crossbar 204 may be a single, integral component. In other instances, the crossbar 204 may be connected to the leg 202A and to the leg 202B.

The example fibula buttons 100A, 100B, or 100C may be composed from any suitable medical-grade material capable of long-term contact with biological materials. For example, the fibula buttons 100A, 100B, or 100C may be composed of nitinol.

Figure 3A:
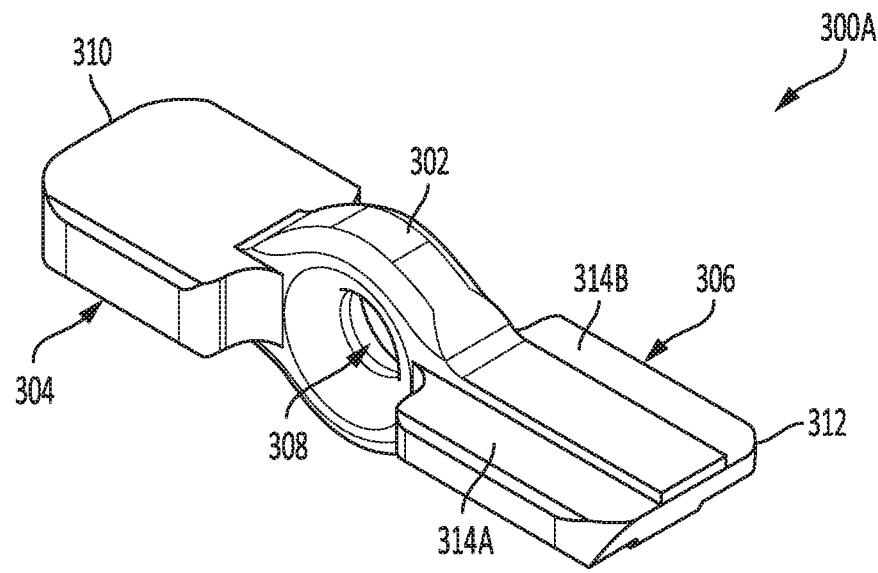
FIGS. 3A and 3B illustrate a perspective and top view, respectively, of a tibia button, according to one aspect of the present disclosure.
Figure 3B:
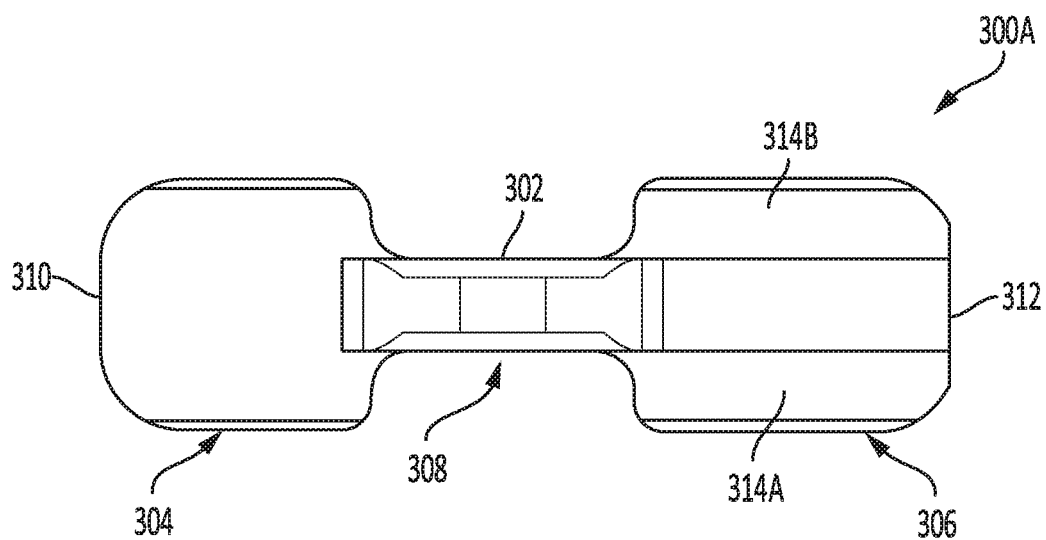
Figure 3C:
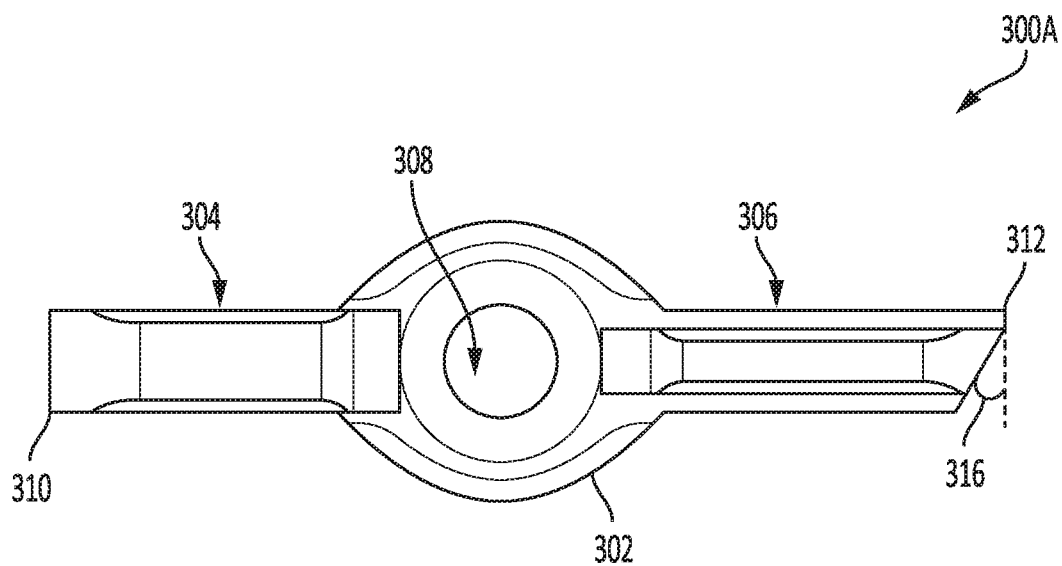
FIGS. 3C and 3D illustrate side views of tibia buttons having inserter ends with different angles, according to one aspect of the present disclosure.

FIGS. 3A, 3B, and 3C illustrate a perspective view, top view, and side view respectively of an example tibia button 300A. The tibia button 300A includes a support 302 having an opening 308. The support 302 may include curved surfaces to reduce friction between suture and the support 302 during installation of the tibia button 300A. In addition, the inclusion of a single opening 308 in the support 302 for each suture strand to move through during installation of the tibia button 300A may help reduce friction between the suture and the tibia button 300A as compared to typical suture buttons having multiple openings for different suture strands or different portions of a single suture strand. A wing 304 extends from the support 302 to a leading end 310 of the tibia button 300A. A wing 306 extends from the support 302 to a chamfered end 312 of the tibia button 300A. The wings 304 and 306 may have various suitable lengths with respect to the support 302.

In various instances, the wing 306 may be configured to engage with a button inserter tip such that the wing 306 does not slide or otherwise move away from the button inserter tip until the tibia button 300A is deployed. For instance, the wing 306 may include recesses 314A, 314B. The wing 306 may include the recesses 314A, 314B on a single side or on opposing sides (e.g., on the opposing side not illustrated). The non-recessed portion(s) of the wing 306 may correspond to a recess or recesses in the button inserter tip such that when the wing 306 is slid within the button inserter tip, lateral movement of the tibia button (e.g., perpendicular to the long axis of the tibia button 300A) is prevented with respect to the button inserter.

Figure 3D:
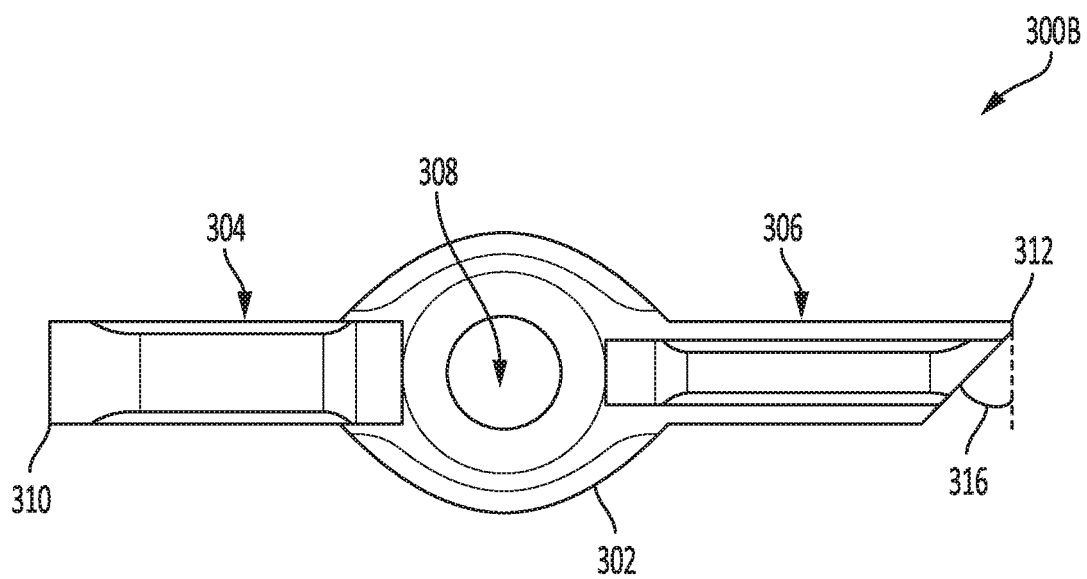

The chamfered end 312 of the wing 306 includes a chamfer at an angle 316. In various examples, the angle 316 may be equal to thirty degrees. In other examples, the wing 306 may be chamfered at another suitable angle 316, such as between 15-60 degrees. For instance, FIG. 3D illustrates an example tibia button 300B having a wing 306 with a chamfered end 312 at an angle 316 of forty-five degrees. The advantages that the chamfered end 312 may provide for the presently disclosed tibia button will be discussed in more detail in connection with FIGS. 6A to 6D.

Figure 3E:
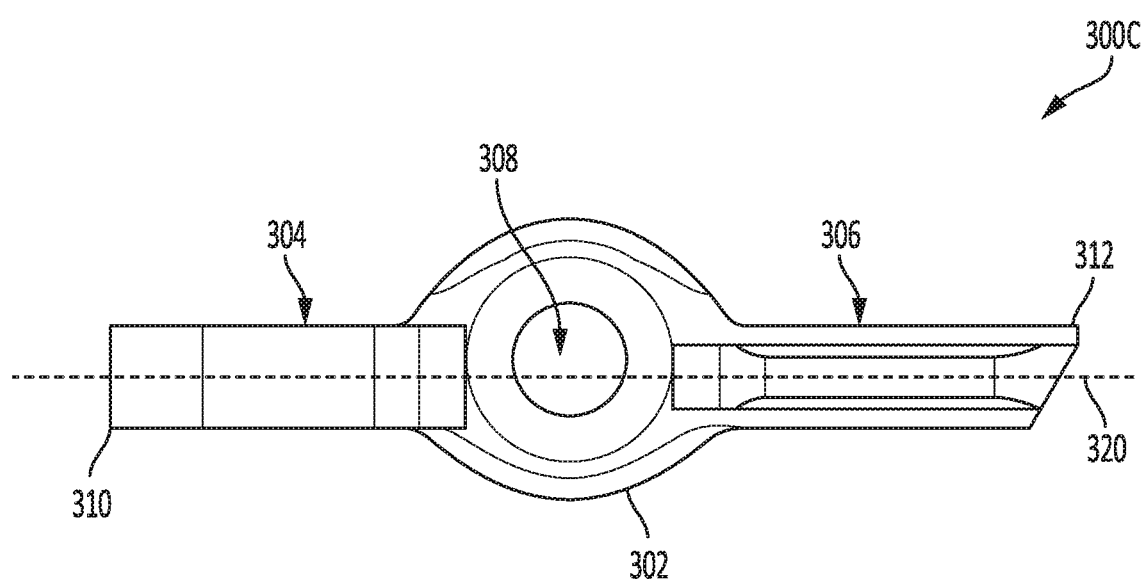
FIG. 3E illustrates a side view of a tibia button having an off-centered opening, according to one aspect of the present disclosure.

In various examples, such as those illustrated in FIGS. 3A to 3D, the support 302 and the opening 308 through the support 302 may be centered relative to the wings 304 and 306. In other examples, the support 302 and/or the opening 308 may be off-center relative to the wings 304 and 306. For instance, FIG. 3E illustrates an example tibia button 300C having a support 302 and an opening 308 that is off-center from an axis 320 of the wings 304 and 306. The support 302 and the opening 308 may be off-center towards the longer side of the wing 306 (e.g., due to the chamfered end 312) to help the tibia button 300C flip into place during installation, as will be described in more detail below. In other examples, the support 302 may be centered while the opening 308 is off-center. In some instances, the support 302 and the opening 308 may be centered along the axis 320 such that the wing 304 and the wing 306 have equal lengths. In other instances, the support 302 and/or the opening 308 may be off-center along the axis 320. When the support 302 is off-center along the axis 320, either the wing 304 or the wing 306 may have a longer length than the other.

The example tibia buttons 300A, 300B, or 300C may be composed from any suitable medical-grade material capable of long-term contact with biological materials. For example, the fibula buttons 300A, 300B, or 300C may be composed of nitinol.

The remaining disclosure will make reference to the example fibula button 100A and the example tibia button 300A. The remaining disclosure, however, may apply equally to the example fibula buttons 100B and 100C, the example tibia buttons 300B and 300C, and any other suitable fibula buttons and/or tibia buttons consistent with the present disclosure.

In some instances, the provided fibula button 100A and/or the provided tibia button 300A may be used with a needle and pull-through suture technique. In other instances, the fibula button 100A and/or the tibia button 300A may be used in conjunction with a button inserter that deploys the fibula button 100A and/or the tibia button 300A for installation in a patient. The fibula button 100A may be used in conjunction with the tibia button 300A in a surgical procedure. The fibula button 100A and the tibia button 300A may alternatively be used independently of one another in a surgical procedure. For instance, the fibula button 100A may be used with a suitable anchor or suture button other than the tibia button 300A. In another instance, the tibia button 300A may be used with a suitable anchor or suture button other than the fibula button 100A.

Figure 4A:
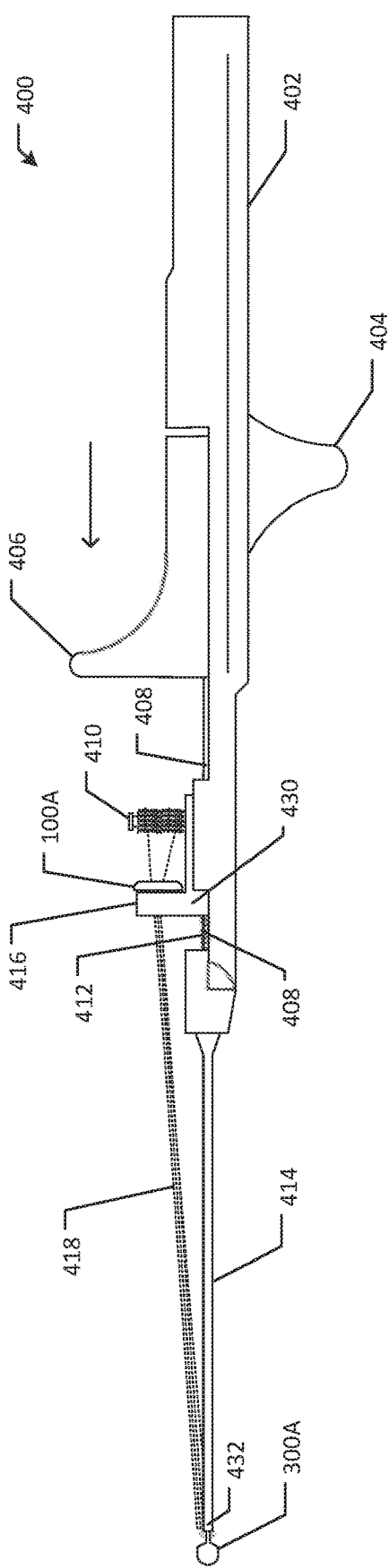
FIGS. 4A and 4B illustrate side views of example systems including a button inserter, suture buttons, and suture, according to one aspect of the present disclosure.

FIG. 4A illustrates an example button inserter 400 that may be used in conjunction with the presently disclosed fibula button 100A and/or tibia button 300A and method. The example button inserter 400 may include a handle 402, a support protrusion 404, a trigger 406, a shaft 414, a pusher rod 408, a resilient member 412 (e.g., a spring), and a button deployer 430. The button deployer 430 may include a suture bollard 410 and a button post 416. In the example, the tibia button 300A is removably engaged with the shaft 414. For example, a portion of the tibia button 300A may be positioned within an insertion tip 432 at the end of the shaft 414 such that the tibia button 300A is constrained rotationally and laterally, as will be described in more detail in connection with FIGS. 6A to 6D. In the illustrated loaded configuration of the example button inserter 400, tension in the suture 418 may secure the tibia button 300A in place along a long axis of the button inserter 400. In some examples, the pusher rod 408 extends from the button deployer 430, through the inside of the shaft 414, to make contact with the tibia button 300A.

The suture 418 may be a flexible material, e.g., suture or suture tape. In some instances, the suture 418 may be a single strand of suture that is arranged to couple the fibula button 100A to the tibia button 300A. In other instances, the suture 418 may be multiple strands of suture that are arranged to couple the fibula button 100A to the tibia button 300A. In at least one instance, the suture 418 can be an adjustable or non-adjustable loop. In at least one instance, the combination of the suture 418, the tibia button 300A, and the fibula button 100A can be an adjustable, knotless button/loop construct. The knotless button/loop construct may be self-locking.

In the loaded configuration of the example button inserter 400, the fibula button 100A may be held against the button post 416 by tension in the suture 418. The suture 418 may be wrapped around the suture bollard 410 prior to deployment. A surgeon, or any other suitable healthcare provider, may use the example button inserter 400 to insert the tibia button 300A through tunnels in a first bone and a second bone (e.g., a fibula and a tibia) and may deploy the tibia button 300A by activating the trigger 406 in the direction of the illustrated arrow. The fibula button 100A may be deployed by translating the button inserter 400 away from the patient. The suture 418 may then be tensioned and secured to install the deployed fibula button 100A and tibia button 300A.

Figure 4B:
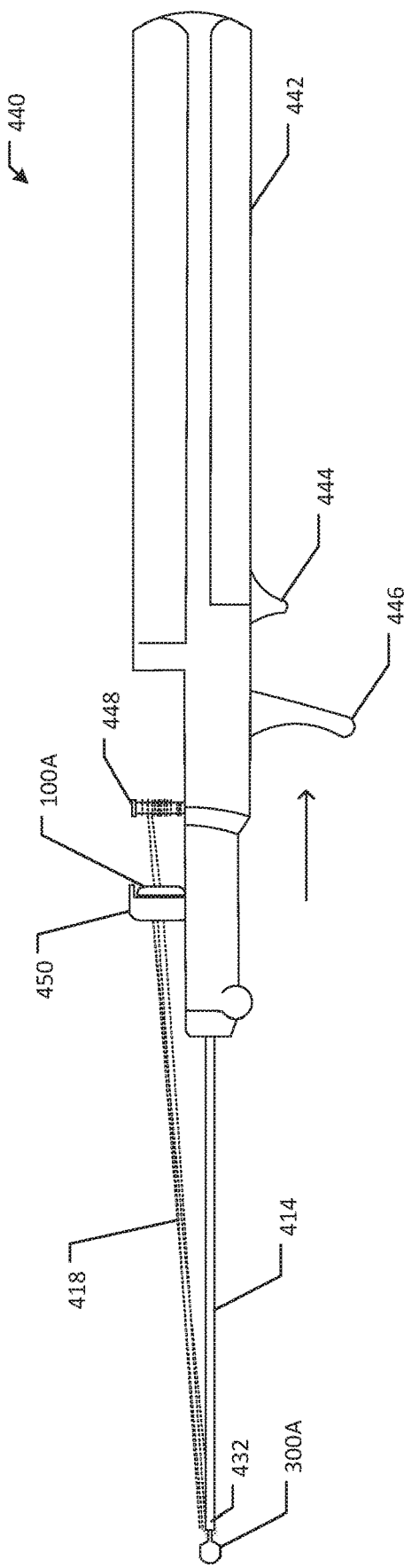

As an alternative to the button inserter 400, FIG. 4B illustrates an example button inserter 440 that may be used in conjunction with the presently disclosed fibula button 100A and/or tibia button 300A and method. The example button inserter 440 includes a handle 442, a support protrusion 444, a trigger 446, an inner rod 508 (FIG. 5), a resilient member 512 (FIG. 5), a shaft 452, and a button deployer 530 (FIG. 5). The button deployer 530 may include a suture bollard 448 and a button post 450. In the example, the tibia button 300A is removably engaged with an insertion tip 432 of the shaft 414 in the same or similar manner as with the example button inserter 400 described above. The example button inserter 440 is configured similarly to the example button inserter 400. A user may activate the trigger 446 by pulling it in the direction of the illustrated arrow to deploy the tibia button 300A. The fibula button 100A may be deployed by translating the button inserter 440 away from the patient.

Figure 5A:
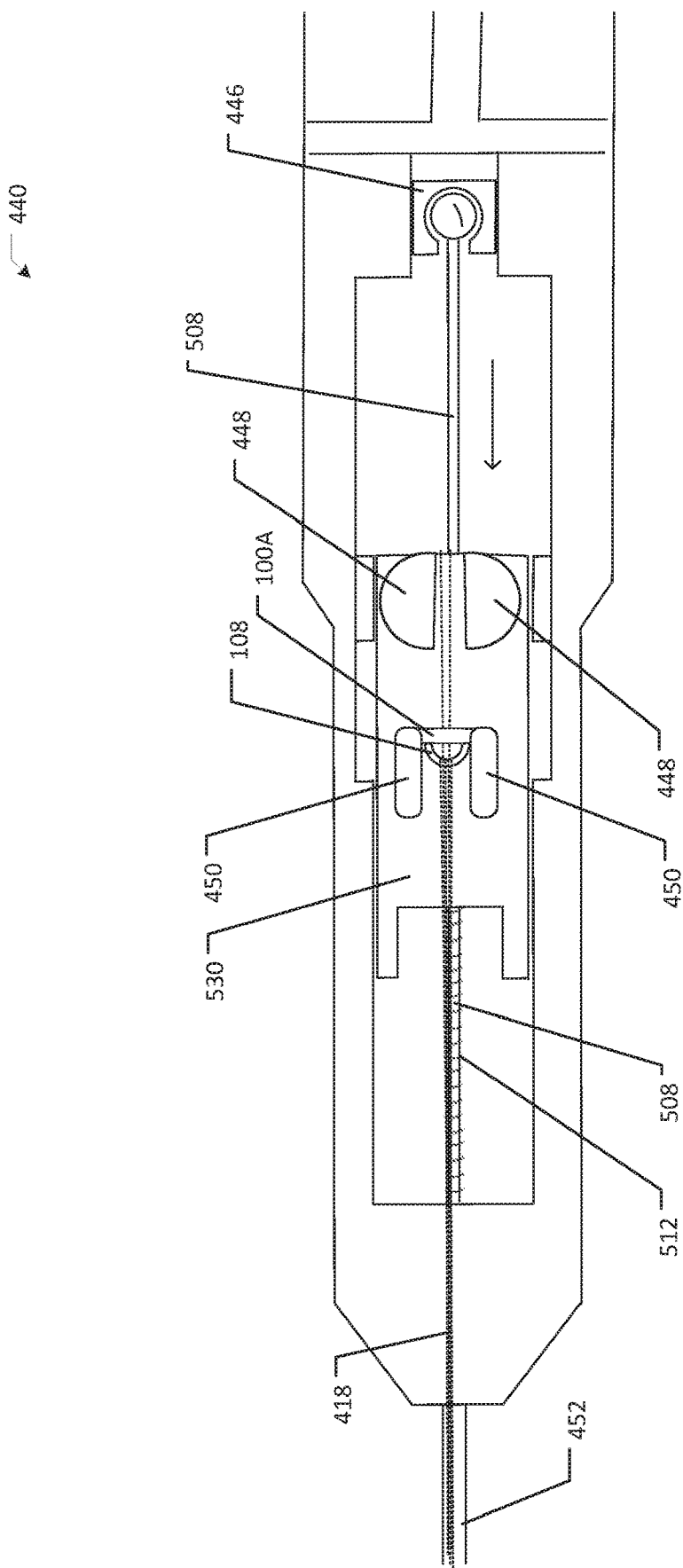
FIG. 5A illustrates a top view of a portion of an example button inserter device loaded with a fibula button, according to one aspect of the present disclosure.

FIG. 5A shows a top view of a portion of the example button inserter 440. The example fibula button 100 is held against the button post 450 by tension in the suture 418. In some examples, the button post 450 includes two separate posts with suitable space in between for the pulley peg 108, as illustrated. This enables the suture 418 to be secured by the pulley peg 108 while also enabling the free ends of the suture 418 to be pulled through the opening 106.

Figure 5B:
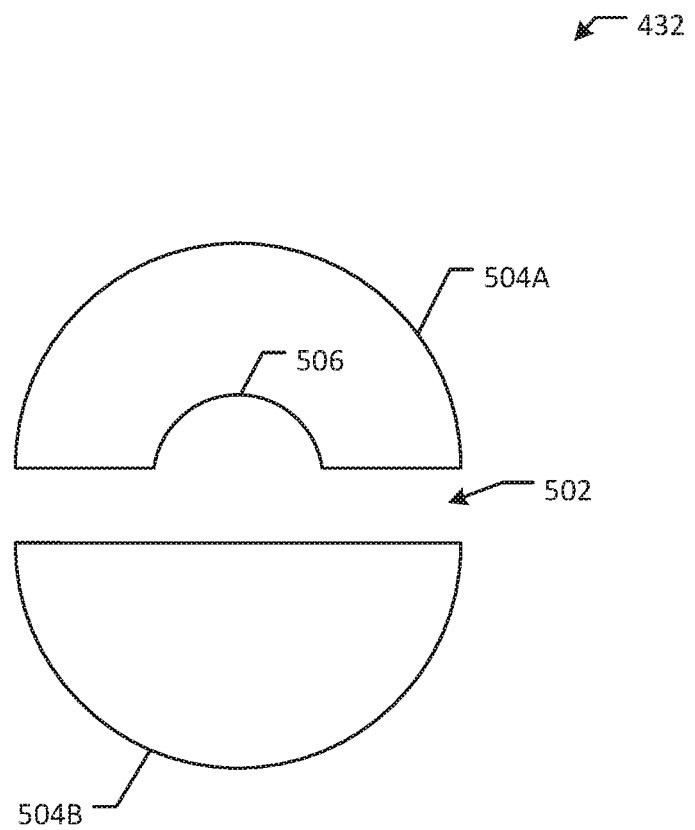
FIG. 5B illustrates a cross-sectional front view of an example insertion tip of a button inserter, according to one aspect of the present disclosure.

FIG. 5B illustrates a cross-sectional front view of an example insertion tip 432 of the button inserter 400 or 440.

The insertion tip 432 may include a slit 502 between a first end 504A and a second end 504B. When a tibia button 300A is positioned within the slit 502, the tibia button 300A is prevented from rotating about its long axis. In some instances, the first end 504A may include a recess 506. The recess 506 may correspond to or line up with a non-recessed portion of the tibia button 300A (e.g., see FIG. 3A) such that the wing 306 of the tibia button 300A may be inserted within the insertion tip 432. For instance, the recess 506 may have a rounded cross-section as illustrated, a squared cross-section, or other suitable shape. The tibia button 300A is accordingly prevented from moving laterally along a short axis of the button inserter 400 or 440 by the non-recessed portion of its wing 306 positioned within the recess 506 of the insertion tip 432. In instances in which the wing 306 of the tibia button 300A includes recesses 314A and 314B on opposing sides, the second end 504B of the insertion tip 432 may include a recess as well. In addition, the recess 506 of the insertion tip 432 prevents the tibia button 300A from rotating about its short axis.

It should be appreciated that the button inserters 400 and 440 are merely examples of button inserters that may be used to deploy the fibula button 100A and/or the tibia button 300A. Any suitable button inserter may be used to deploy the fibula button 100A and/or the tibia button 300A that is compatible with the advantages of the fibula button 100A and/or the tibia button 300A as described herein.

Figure 6A:
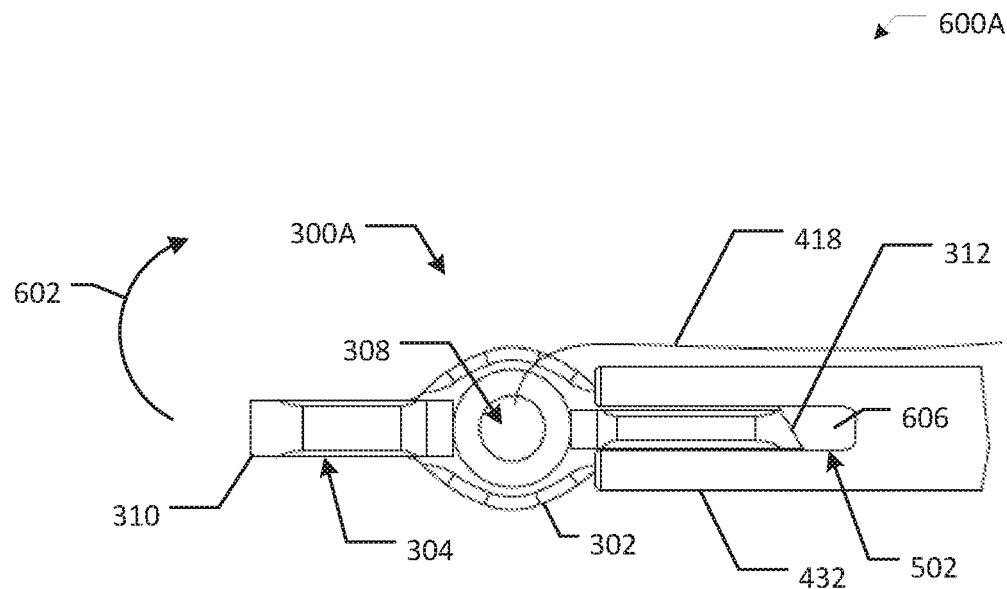
FIGS. 6A and 6B illustrate perspective side views of a tibia button loaded into an insertion tip of a button inserter, according to one aspect of the present disclosure.
Figure 6B:
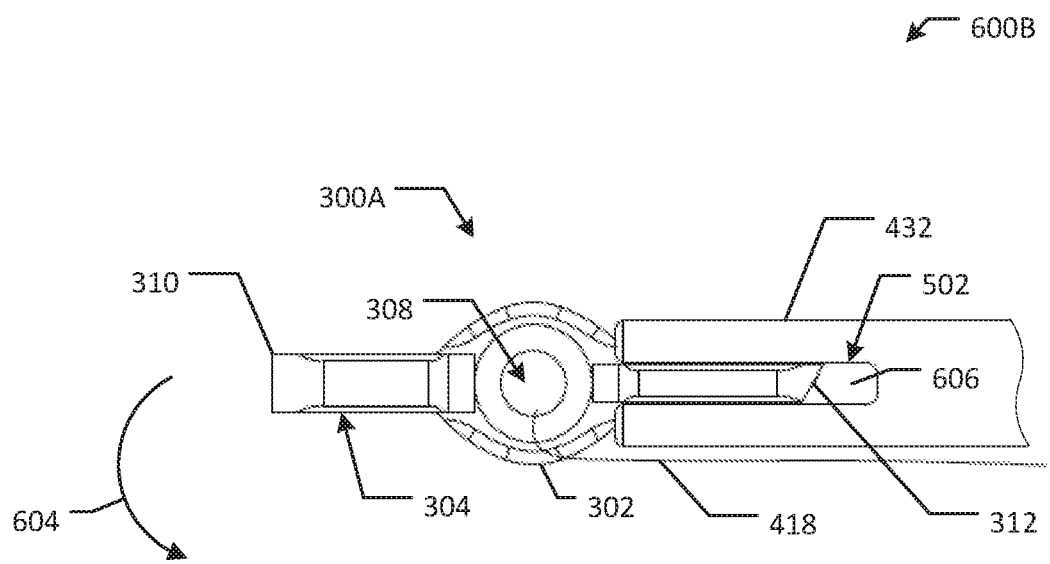

FIGS. 6A and 6B illustrate perspective side views of alternate configurations of the tibia button 300A loaded within the insertion tip 432 of a button inserter (e.g., the button inserter 400). In the configuration 600A shown in FIG. 6A, the tibia button 300A is positioned with in the insertion tip 432 such that the chamfered end 312 is facing a first direction (e.g., towards the top of the page). In the configuration 600B shown in FIG. 6B, the tibia button 300A is positioned within the insertion tip 432 such that the chamfered end 312 is facing opposite of the first direction (e.g., towards the bottom of the page). In each of the configurations 600A and 600B, the chamfered end 312 is facing towards the suture 418. The chamfered end 312 facing towards the suture 418 helps facilitate the tibia button 300A flipping into place in a desired direction once the tibia button 300A is deployed. For instance, in the configuration 600A, the tibia button 300A flips in the direction of the arrow 602 upon deployment. Conversely, in the configuration 600B, the tibia button 300A flips in the direction of the arrow 604 upon deployment.

In either the configuration 600A or 600B, the configuration of the tibia button 300A enables the suture 418 to be to the side of the insertion tip 432 and button inserter shaft, rather than the suture 418 winding around the button inserter shaft or around the tibia button 300A itself. In addition, the tibia button 300A and the insertion tip 432 may be constructed such that a gap 606 remains between the tibia button 300A and the insertion tip 432 when the tibia button 300A is fully inserted. The gap 606 is radiolucent and is therefore visible under x-ray. The gap 606 may help a surgeon guide how far the button inserter must be inserted before deploying the tibia button 300A.

Figure 6C:
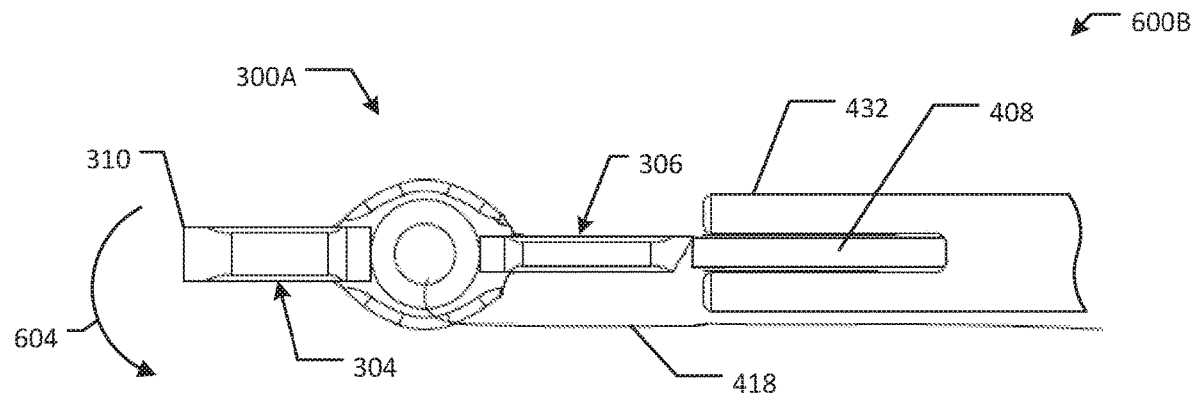
FIGS. 6C and 6D illustrate perspective side views of the button inserter of FIG. 6B deploying the tibia button, according to one aspect of the present disclosure.
Figure 6D:
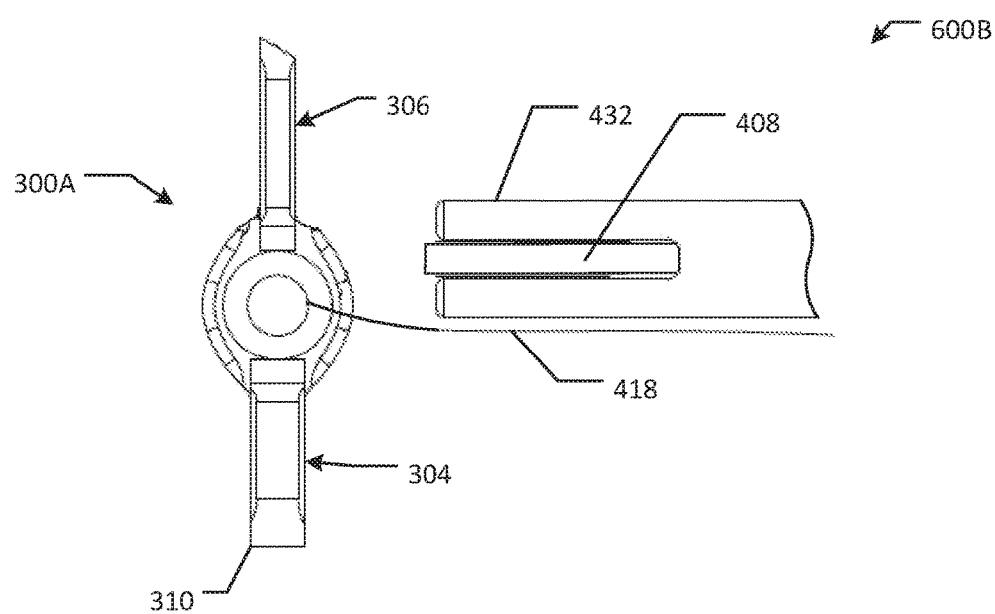

FIGS. 6C and 6D further illustrate the configuration 600B to show an example of the tibia button 300A flipping into place upon deployment. FIG. 6C illustrates that the pusher rod 408 of the example button inserter 400 translates to push the tibia button 300A out of the insertion tip 432. For instance, activating the trigger 406 of the button inserter 400 may translate the pusher rod 408. In various instances, the pusher rod 408 may extend beyond the end of the insertion tip 432 when the trigger 406 is fully depressed, which may help ensure that the tibia button 300A is fully separated from the button inserter 400 and pushed all the way out of the insertion tip 432. Ensuring that the tibia button 300A is fully separated from the button inserter 400 may allow for easier deployment when installation of the tibia button 300A involves pushing against resisting tissue (e.g., skin). In addition, the end of the pusher rod 408 that contacts the tibia button 300A may be flat, as illustrated, such that it only contacts the nearest portion of the chamfered end 312. The space between the flat end of the pusher rod 408 and the chamfered end 312 of the tibia button 300A allows space for the tibia button 300A to rotate or flip.

Upon the tibia button 300A being pushed all the way out of the insertion tip 432, tension in the suture 418 causes the tibia button 300A to flip to the side of the suture 418 (e.g., in the direction of the arrow 604). The chamfered surface 312 of the tibia button 300A and the minimal contact between the pusher rod 408 and the chamfered surface 312 help facilitate the tibia button 300A flipping towards the side of the suture 418. Facilitating the tibia button 300A flipping in a desired or target direction may help reduce complications during a surgical procedure that may arise by the tibia button 300A flipping in an undesired direction, which may potentially cause the suture 418 to tangle or get pinched. The provided flipping facilitation of the present disclosure also enables the tibia button 300A to flip very close to the insertion tip 432, which can increase the ease of deploying the tibia button 300A. FIG. 6D shows the flipped tibia button 300A.

Figure 7:
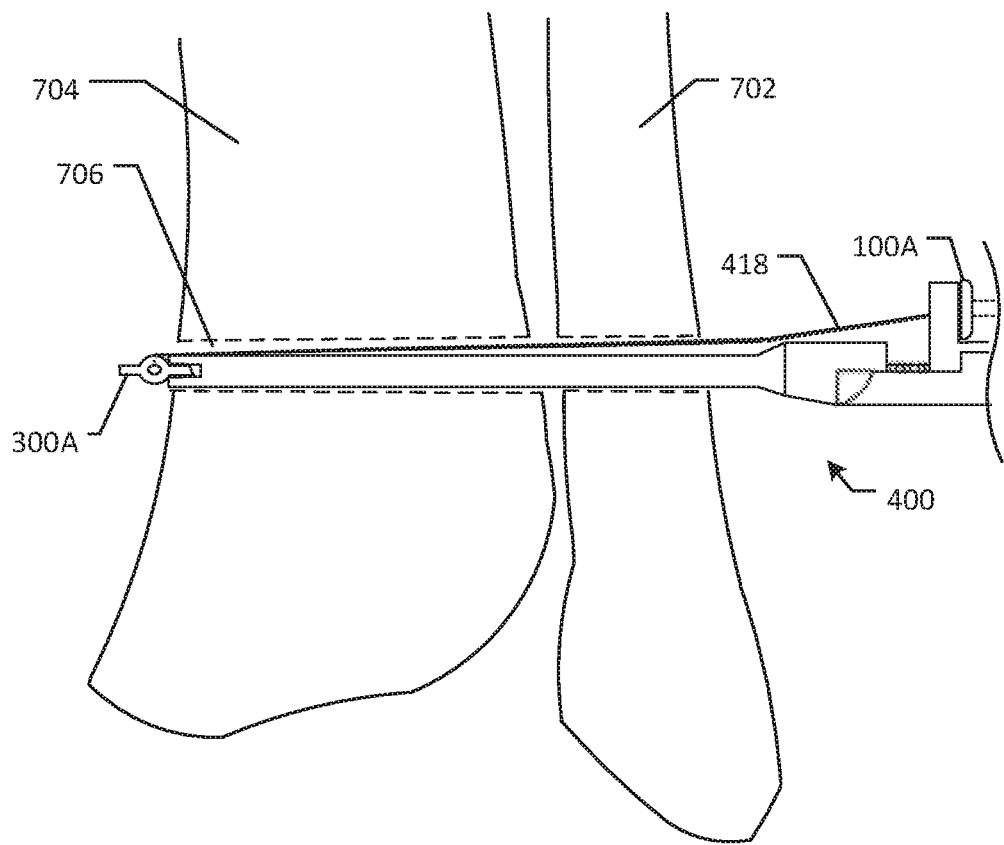
FIG. 7 illustrates a button inserter, loaded with a fibula button and tibia button, positioned through a bone hole to transport the tibia button to the other side of the bone hole, according to one aspect of the present disclosure.

As indicated, the fibula button 100A and the tibia button 300A may be utilized as part of the suture-button technique to secure two bones together. For example, a method of ankle syndesmosis repair (with or without ankle fracture) may include drilling a bone hole through a patient's fibula and tibia. A button inserter (e.g., the button inserter 400) may be loaded with the tibia button 300A and the fibula button 100A. A surgeon may transport the tibia button 300A through the bone hole via the button inserter. FIG. 7 illustrates the tibia button 300A transported through a bone hole 706 in a fibula bone 702 and a tibia bone 704 via the button inserter 400. Suture 418 couples the tibia button 300A to the fibula button 100A. A surgeon may then deploy the tibia button 300A and the fibula button 100A, such as by activating the trigger 406 on the button inserter 400 and then translating the button inserter 400 away from the patient. In some instances, the tibia button 300A may deploy first, and then the fibula button 100A may be deployed once the tibia button 300A is in position.

Figure 8:
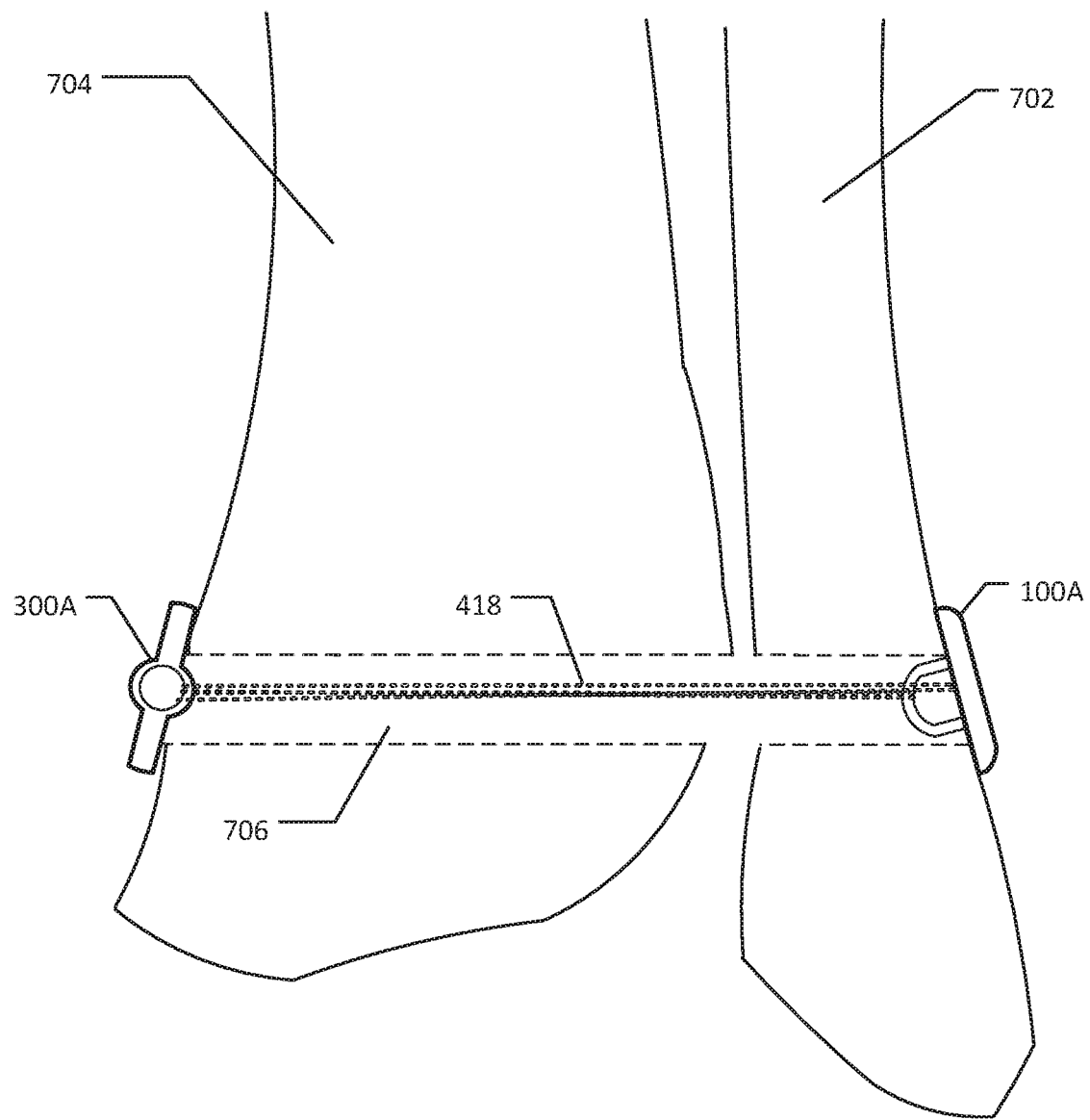
FIG. 8 illustrates an installed fibula button and a tibia button securing two bones together, according to one aspect of the present disclosure.

Upon deployment, the tibia button 300A flips as described above and contacts the surface of the tibia bone 704. The surgeon may remove the button inserter 400 from the bone hole 706. The surgeon may tension the suture 418 (e.g., cinch an adjustable construct) to position the fibula button 100A and secure it against the lateral surface of the fibula bone 702. Once the tibia button 300A and the fibula button 100A are in position, the suture 418 may be secured, such as by a knot or via a knotless button-loop construct. The free ends of the suture 418 may be trimmed to remove excess material. FIG. 8 illustrates an installed fibula button 100A and tibia button 300A coupled by suture 418 and securing the fibula bone 702 to the tibia bone 704. The pulley peg 108 of the fibula button 100A is fully within the bone hole 706, which enables solely the button head 102 of the fibula button 100A to protrude from the surface of the fibula bone 702. In some instances, a knot of suture 418 may be positioned within the opening 106 of the fibula button 100A.

The examples and embodiments disclosed herein are to be construed as merely illustrative and not a limitation of the scope of the present disclosure in any way. It will be apparent to those having skill in the art that changes may be made to the details of the above-described embodiments without departing from the underlying principles discussed. In other words, various modifications and improvements of the embodiments specifically disclosed in the description above are within the scope of the appended claims. For example, any suitable combination of features of the various embodiments described is contemplated.

The invention is claimed as follows:

1. A suture button for aiding in fixation of two bones, the suture button comprising:
   a head having a rounded top surface, a flat bottom surface, and a first opening extending through the head from the rounded top surface to the flat bottom surface; and
   a pulley peg elongated from a first end to a second end, the first and second ends each connected to the flat bottom surface of the head so as to form a second opening between the pulley peg and the bottom surface of the head, wherein at least a portion of an inner portion of the head that forms the first opening continues directly into the pulley peg, such that the inner portion of the head that forms the first opening lies on a same plane as an inner portion of the pulley peg.

2. The suture button of claim 1, wherein the first opening has a circular cross section.

3. The suture button of claim 1, wherein the first opening has a pill-shaped cross section.

4. The suture button of claim 3, wherein the pill-shaped cross section of the first opening defines a longitudinal direction and extends in the longitudinal direction, and wherein a plane extending through the first and second ends of the pulley peg is substantially perpendicular to the longitudinal direction.

5. The suture button of claim 1, wherein the rounded top surface includes a chamfer leading to the first opening.

6. The suture button of claim 1, wherein the pulley peg includes at least one flat surface near each of the first end and the second end.

7. The suture button of claim 1, wherein the pulley peg is rounded at each of the first end and the second end nearest the first opening.

8. The suture button of claim 1, wherein the pulley peg is a single, continuous piece of material.

9. The suture button of claim 8, wherein a portion of the pulley peg furthest from the bottom surface is rounded.

* * * * *